United States Patent [19]

Ideker et al.

[11] Patent Number: 4,827,932
[45] Date of Patent: May 9, 1989

[54] IMPLANTABLE DEFIBRILLATION ELECTRODES

[75] Inventors: Raymond E. Ideker, Durham, N.C.; Michael J. Fine, Lake Jackson, Tex.; Ross G. Baker, Jr.; Richard V. Calfee, both of Houston, Tex.

[73] Assignee: Intermedics Inc., Angleton, Tex.

[21] Appl. No.: 19,670

[22] Filed: Feb. 27, 1987

[51] Int. Cl.⁴ ............................................. A61N 1/36
[52] U.S. Cl. .............................. 128/419 D; 128/642; 128/644; 128/784; 128/785; 128/798
[58] Field of Search ........... 128/639, 642, 644, 419 D, 128/419 P, 784, 785

[56] References Cited

U.S. PATENT DOCUMENTS

| | | | |
|---|---|---|---|
| 3,685,645 | 8/1972 | Kawaguchi | 128/419 D |
| 4,030,509 | 6/1977 | Heilman et al. | 128/419 D |
| 4,291,707 | 9/1981 | Heilman et al. | 128/419 D |
| 4,628,937 | 12/1986 | Hess et al. | 128/642 |

*Primary Examiner*—Francis Jaworski
*Assistant Examiner*—Timothy Keegan
*Attorney, Agent, or Firm*—Russell J. Egan; Donald R. Greene

[57] ABSTRACT

A pair of defibrillation patch electrodes is adapted for close fitting placement over the ventricles of the heart, either epicardially or pericardially. One of the patches is contoured to fit over the right ventricle, and the other is contoured to fit over the left ventricle in spaced relationship to the first patch to form a substantially uniform gap between confronting borders of the two. The gap is sufficiently wide to avoid the shunting of current between edges of the patches upon delivery of defibrillation shocks, as well as to accommodate the ventricular septum and the major coronary arteries therein. The size and shape of the patches is such that they encompass most of the ventricular myocardium within and between their borders, to establish a nearly uniform potential gradient field throughout the entire ventricular mass when a defibrillation shock is delivered to the electrodes. Flat versions of the two electrodes provide ease of manufacture.

20 Claims, 4 Drawing Sheets

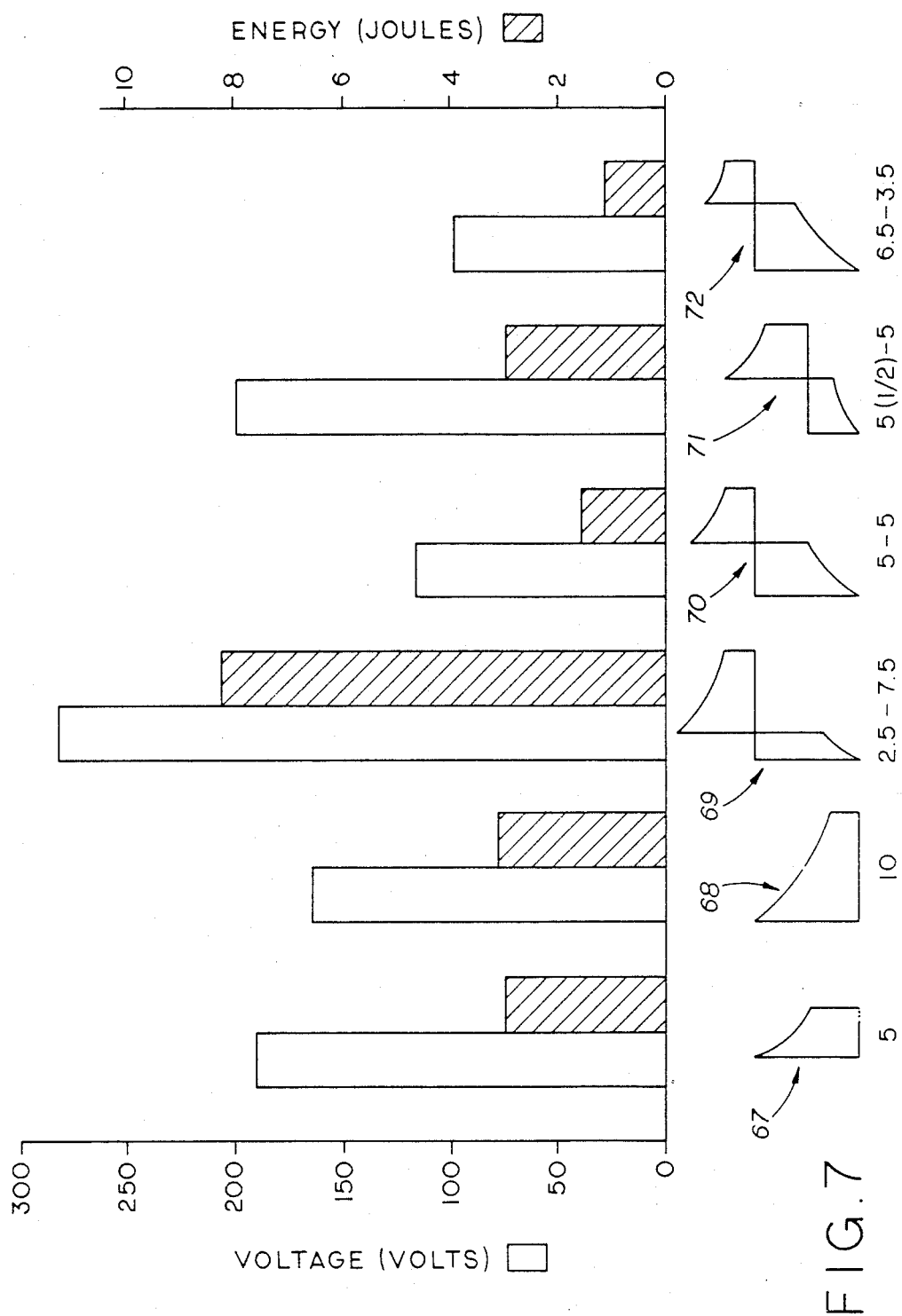

IMPLANTABLE DEFIBRILLATION ELECTRODES

BACKGROUND OF THE INVENTION

1. Field of the Invention

The present invention relates generally to medical devices, and more particularly to patch electrodes for use with automatic implantable cardiac defibrillators.

2. Relevant Background

Cardiac arrhythmias can arise in the atria or ventricles as a consequence of an impairment of the heart's electrophysiologic properties such as excitability, conductivity, and automaticity (rhythmicity). Tachycardia is an arrhythmia characterized by rapid beating of the affected chamber which, in some instances, may lead to fibrillation. During fibrillation, sections of conductive cardiac tissue of the affected chamber undergo completely uncoordinated random contractions, quickly resulting in a complete loss of synchronous contraction of the overall mass of tissue and a consequent loss of the blood-pumping capability of that chamber.

Because of the lack of contribution of the atrial chambers to cardiac output, atrial fibrillation is hemodynamically tolerated and not generally regarded as life-threatening. However, in the case of ventricular fibrillation, cardiac output ceases instantaneously as a result of the rapid, chaotic electrical and mechanical activity of the excitable myocardial tissue and the consequent ineffectual quivering of the ventricles. Unless cardiac output is restored almost immediately after the onset of ventricular fibrillation, tissue begins to die for lack of oxygenated blood, and death will occur within minutes.

Ventricular fibrillation is frequently triggered by acceleration of a ventricular tachycardia. Hence, various methods and devices have been developed or proposed to treat and arrest the tachycardia before the onset of fibrillation. Conventional techniques for terminating tachycardia include pacing therapy and cardioversion. In the latter technique, the heart is shocked with one or more current or voltage pulses of generally considerably higher energy content than is delivered in pacing pulses. Unfortunately, the use of such therapy itself presents a considerable risk of precipitating fibrillation.

Defibrillation—that is, the method employed to terminate fibrillation—involves applying one or more high energy "countershocks" to the heart in an effort to overwhelm the chaotic contractions of individual tissue sections and to re-establish an organized spreading of action potential from cell to cell of the myocardium, thereby restoring the synchronized contraction of the mass of tissue. If these chaotic contractions continue in any tissue section, the defibrillation may be short-lived in that the uncontrolled tissue section remains a potential source for re-fibrillation. Successful defibrillation clearly requires the delivery of a shocking pulse containing a substantial amount of electrical energy to the heart of the afflicted person, at least adequate to terminate the fibrillation and the preclude an immediate re-emergence.

In the conventional approach of transthoracic external defibrillation, paddles are positioned on the patient's thorax and, typically, from about 100 to about 400 joules of electrical energy is delivered to the chest area in the region of the heart. It is apparent from the manner in which the shock is applied that only a portion of this energy is actually delivered to the heart and, thus, is available to arrest fibrillation. Where fibrillation occurs during open heart surgery, internal paddles may be applied to opposite surfaces of the ventricular myocardium and, in these instances, the energy required to be delivered is considerably less, on the order of 20 to 40 joules.

Over the past several years, implantable automatic defibrillators have been developed for use in detecting and treating ventricular fibrillation. In 1970, M. Mirowski et al. and J. C. Schuder et al. separately reported in the scientific literature their independent proposals for a "standby automatic defibrillator" and a "completely implanted defibrillator", respectively, including experimental results in dog tests. Since that time, a vast number of improvements in implantatable defibrillators, including electrode placement using extraperidcardial patches or transvenous catheter, has been reported in the scientific literature and patent publications.

The pulse energy requirements for internal defibrillation with known implantatable defibrillators and electrode systems range from about 5 joules to approximately 40 joules. Of course, the actual energy level required may differ from patient to patient, and further depends on such factors as the type of pulse waveform and the electrode configuration employed. While advances and improvements in electrical energy sources in general and pacemaker batteries in particular have been made over the past few years, it is clear, nonetheless, that repeated delivery of such amounts of energy from an implanted system will deplete conventional batteries in relatively short order. Accordingly, reduction of the energy level required for internal defibrillation remains a key area of inquiry and investigation.

It is a principal object of the present invention to provide improvements in electrode systems for internal defibrillation and in methods for making such electrode systems.

A related object is to provide an implantable electrode system, for use with implantable automatic defibrillators, which delivers the defibrillating waveform with considerably greater efficiency than has been achieved using prior art systems, and which therefore provides successful defibrillation at markedly reduced levels of electrical energy, compared to the levels heretofore necessary.

An early U.S. patent, in terms of the relative immaturity of developments in the field, U.S. Pat. No. 2,985,172, issued in 1961, described a tissue contact electrode for use in delivering a high voltage discharge directly to the heart. Each electrode consisted of a conductive ring connected to an insulated electrical lead, the ring holding conductive foil members and enclosed in a gauze sock, with a flexible backing member at one side of the gauze sheath. The overall electrode pad was described as sufficiently flexible to assume a dished shape tightly engaging the tissue of the heart.

In U.S. Pat. No. 4,030,509, Heilman et al. described an implantable electrode system for ventricular defibrillation, in which the electrodes are arranged in a generally base-apex configuration with a split conformal base electrode positioned above the base of the ventricles in the region of the atria, and a cuplike conformal apex electrode positioned at the apex of the heart.

In U.S. Pat. Nos. 4,270,549 and 4,291,707, Heilman et al. disclosed defibrillation electrodes of rectangular shape designed for insertion through the soft tissues outside the pleural cavity for contacting the heart. Each electrode consists of a metallic mesh either sandwiched between two layers of inert electrical insulation material or backed with a single layer of such material stitched to the mesh.

In U.S. Pat. No. 4,548,203, Tacker et al. disclosed an electrode system for use with implantable pulse generators employed for cardioversion or defibrillation. The system consists of two sets of opposed patch electrodes, one pair disposed laterally on the epicardium and the other pair disposed ventrally-dorsally, with each electrode orthogonal to the adjacent electrodes. The patent asserts that the presence of the latter pair of electrodes does not significantly alter the current distribution from the first pair, so long as the electrodes are relatively small with respect to the epicardial circumference and the two pairs are isolated from each other during current flow. The patent further ascribes the use of two pairs of electrodes implanted in spaced relationship as purportedly permitting the use of smaller electrodes, lower voltage and current, and lower total energy, with a more uniform current density and less hazard of damage to adjacent heart tissue, than had theretofore been achieved. Two current pulses are sequentially delivered to the separate pairs of electrodes to provide a temporal and spatial summation effect for the defibrillating current.

Nevertheless, these and other prior art electrode systems proposed for use with implantable defibrillators dissipate relatively large amounts of energy in delivering shocking pulses to the heart. Consequently, their performance tends to be marred by unacceptably high risk of damage to the myocardium, and by the need for relatively large sized defibrillation pulse generators (including batteries) to supply the high energy levels required over even somewhat short term use.

A reduction in the shock strength required for defibrillation would be advantageous in that it would allow for a decrease in the size of the automatic implantable defibrillator, an increase in battery life, and a reduction of the possibility of myocardial damage resulting from the shock.

SUMMARY OF THE INVENTION

The present invention provides improvements in implantable electrodes, and in methods of making such electrodes, for delivery of defibrillating waveforms to a heart in ventricular fibrillation, and in apparatus and methods for defibrillation. It has been observed that the electrical potential gradient field created from shocks through small epicardial defibrillation electrodes is extremely uneven, with the highest potential gradient occurring near the electrodes, and the lowest potential gradients occurring in areas distant from the electrodes. Following application of a shock just below the defibrillation threshold to a heart in ventricular fibrillation, which is unsuccessful to terminate the fibrillation, the site of earliest resumption is observed to be in an area of low potential gradient, distant from the electrodes. However, a shock which creates a field just strong enough to defibrillate in regions distant from the electrodes will establish a much stronger field near the electrodes. At best, this is wasteful of the limited energy available in an implantable system, and, at worst, may cause myocardial damage and cardiac arrhythmias. Accordingly, we postulate that a more uniform potential gradient field would improve efficiency of the energy delivery system and reduce the energy required for successful defibrillation.

According to a major aspect of the invention, separate large area defibrillation patch electrodes are placed over the right ventricle and the left ventricle of the heart and secured directly to either the epicardium or the pericardium. Each electrode is fabricated from a conductive layer, such as a mesh, with a bio-compatible insulative backing layer overlying one side of the conductive mesh, and an electrically conductive connection between the mesh and a lead for delivering the defibrillating waveform from the implanted (or external) defibrillator to the electrode. Preferably, each electrode is contoured to conform to the shape of the heart in the region of the respective ventricle over which it is to be placed, and has a size and shape to encompass a substantial portion of the ventricular myocardium but not other areas of the heart. In alternative embodiments of the invention, however, the electrodes are fabricated in a flat configuration, also of a size and shape such that when placed over the respective ventricles they encompass a substantial portion of the ventricular myocardium, despite some deformation of each electrode.

One significant principle applied in the design of the electrodes of the invention is that a more uniform potential gradient field should be provided throughout the entire ventricular mass. Electrodes of large surface area appear to be conducive to a more even field, and to decreased electrode impedance. Important criteria relating to the structure and placement of patch electrodes according to the invention, include the following: (1) The electrodes should be of a size and shape such that they may be placed to encompass all or a substantial portion of the ventricular myocardium within their borders, while at the same time, the size, shape and placement should provide a gap between the confronting borders of the electrodes which is sufficiently wide to preclude the likelihood that current will be shunted between the electrode edges. (2) The size and shape of the electrodes should further be such that when properly placed over the ventricles, the gap between their confronting borders is substantially uniform throughout the region of the confrontation. (3) The gap should be sufficient to accommodate the ventricular septum therein, when the electrodes are in place over the ventricles, such that the preferential flow of current is through one ventricle and across the septum to the free wall of the other ventricle, to preclude flow along the high conductivity blood cavities of the ventricles. (4) The gap should also be sufficient, when the electrodes are in place over the ventricles, to accommodate the major coronary arteries therein, and thereby reduce the likelihood of vascular injury from subjection to high field intensity during delivery of the defibrillating waveform.

BRIEF DESCRIPTION OF THE DRAWINGS

The above and still further objects, features and attendant advantages of the present invention will become apparent to those persons skilled in the field to which the invention pertains from a consideration of the following detailed description of a presently preferred embodiment, taken in conjunction with the accompanying drawings, in which:

FIGS. 6a, 6b and 6c are plan views of flat patch electrodes according to an alternative embodiment of the invention, in which FIG. 6a illustrates a right ventricular electrode, and FIGS. 6b and c illustrate alternative forms of a left ventricular electrode; and FIG. 7 is a set of histograms of defibrillation threshold voltage and energy for six waveforms, some of which were used with epicardial placement and others with pericardial placement of the patch electrodes of FIG. 1, in tests conducted on six dogs.

DETAILED DESCRIPTION OF A PREFERRED EMBODIMENT

Referring now to FIGS. 1a, 1b, 2a, 2b, and 4, in a preferred embodiment of the invention a pair of contoured defibrillation patch electrodes 12 and 15 are configured with relatively large surface area compared to prior art forms of defibrillation patch electrodes. In particular, each of patch electrodes 12 and 15 is contoured to conform to the shape of the heart in the region of the right and left ventricles of the heart 10, respectively, for placement over the ventricles on the epicardium or the pericardium. After proper placement on the epicardium, for example, as generally ilustrated in FIGS. 1a and 1b (the former being the anterior and the latter the posterior representation), the two patch electrodes 12 and 15 may be secured directly to the epicardium by sutures.

Figure 4:
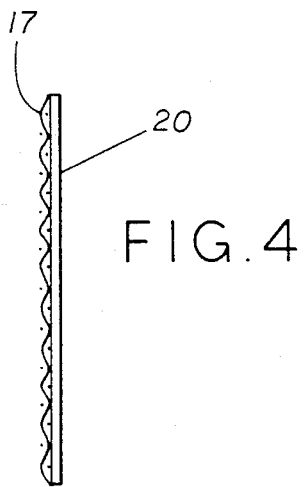
FIG. 4 is a section view taken through a patch electrode according to the invention.

Preferably, each patch electrode is fabricated from a conductive mesh 17, such as titanium mesh grade 2 having 50 by 50 lines per inch (available, for example, from Unique Wire of Hillside, N.J.), with a conformal (flexible) biocompatible insulative backing layer 20, such as 0.020 inch thick silicone rubber sheet, adherently secured to the mesh (FIG. 4). The conductive mesh 17 will lie closest to the heart when the patch electrode is positioned for delivering defibrillating waveforms to the heart.

Figure 5:
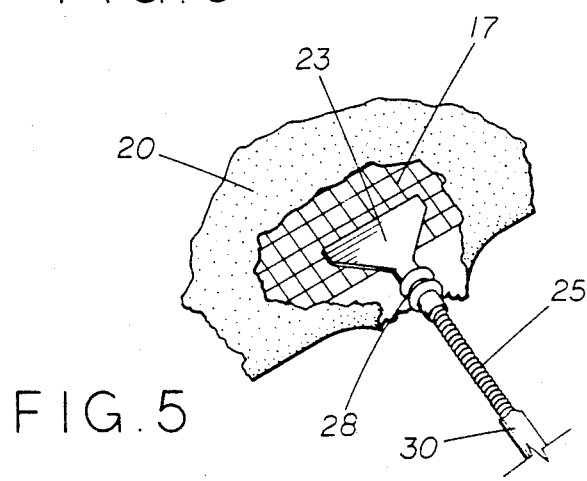
FIG. 5 is a fragmentary view, partly broken away, illustrating the connection between a patch electrode and an electrical lead, according to an embodiment of the invention.

Each patch electrode may be fabricated manually using a model of the heart on which the layers are stretched and molded, or, for ease of manufacture, by sandwiching the layers between two halves of a heart-shaped mold. In either event, the conductive mesh 17 and insulative sheet 20 are cut or punched to proper size and shape according to the design principles to be described presently. The two layer assembly is then cured at a temperature of 325 degrees F. for a period of about 25 minutes. A pair of tabs 23 (FIG. 5), preferably of titanium, may be spot welded to both sides of the mesh 17 at an edge location selected for connecting a low impedance coil lead 25 to the respective patch electrode, before the curing step, or afterward if the insulating backing 20 is then removed from the mesh at the point selected for the connection. Coil lead 25 may be tantalum-clad zirconium copper (from Heraeus of West Germany). The pair of tabs 23 mate together forming a hole into which coil lead 25 is readily inserted with a close tolerance. A crimp sleeve 28, also composed of titanium, is then placed over the ends of the pair of tabs forming the hole into which the coil lead is inserted, and the sleeve 28 is then crimped to assure a good electrical connection between the conductive layer (mesh 17) of the patch electrode and lead 25. A biocompatible insulative tube 30, preferably of 80 durometer silicone rubber, is then placed over the entire length of the coil lead.

Preferably, the entire border of the multilayer patch electrode is covered with a strip of biocompatible insulative sheet 33, such as Dow Corning 501-1 reinforced silastic sheeting (Dacron mesh), and glued in place with a suitable biocompatible medical grade adhesive such as Dow Medical Adhesive Silicone Type A (FIG. 2). This silastic mesh border forms a convenient area for suturing the patch electrode, which might otherwise rupture from the sutures, in place over the respective ventricle. After the insulative border mesh 33 is secured to the patch, it is preferable that additional layers of silicone rubber be applied to provide strain relief at the site 35 of the lead connection as shown in FIG. 2. The patch electrode portion of the assembly should be recured at a temperature of 325 degrees F, for about 15 to 20 minutes after each layer of insulative rubber is applied, and should undergo a final postcure at the same temperature for a period of approximately four hours.

Figure 3:
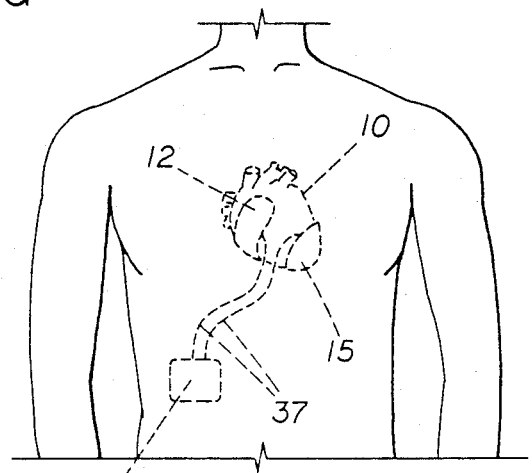
FIG. 3 is a diagrammatic representation of a portion of the human body illustrating the patch electrodes connected to an implanted automatic defibrillator.

As illustrated in FIG. 3, the patch electrodes 12 and 15 are sutured in place over the ventricles (in thoracic surgery involving opening of the patient's chest), and the leads 37 are connected (using conventional connectors 38, FIG. 2b) to an implanted automatic defibrillator 39.

An important principle applied in the design of patch electrodes 12, 15 is that the two electrodes, when in place over the respective ventricles, should encompass a substantial portion of the ventricular myocardium between the electrode pair, which, according to our results, appears to establish a more uniform potential gradient field throughout the entire ventricular mass than has heretofore been achieved with patch or other defibrillating electrodes of other configurations. While we are not absolutely certain of all of the mechanisms leading to the improved results obtained with patch electrodes according to the present invention, it is believed that electrodes of such relatively large surface area serve to create a more even electric field, as well as to decrease the electrode impedance.

Another important aspect of the electrode design according to the invention is that patch electrodes, although sized and shaped to encompass all or substantially all of the ventricles between them (and to avoid other regions of the heart), should have a relatively uniform gap 40 (FIG. 1) maintained between their confronting borders, and throughout the region of the confrontation, when the electrodes are in place over the respective ventricles. This gap 40 should be sufficiently wide to eliminate or considerably reduce the likelihood that current will be shunted between the confronting electrode edges when defibrillating shocks are applied. Thus, a balance must be struck to provide a pair of large area electrodes which will at one and the same time establish the desired more uniform field through the ventricles and yet have their opposing borders as far apart as possible to avoid a loss of current flow across the base of the heart and a consequent reduction in the efficient delivery of energy to terminate the fibrillation.

Further, the substantially equidistant spacing between confronting borders of the two patch electrodes (i.e., gap 40) should be sufficiently wide that the interventricular septum is accommodated within the gap. As a consequence, current will flow preferentially through one ventricle across the septum to the free wall of the other ventricle, rather then along the high conductivity blood cavities of the ventricles. Also, as will be observed from FIGS. 1a and 1b, the gap should accommodate some major coronary arteries, such as the left anterior descending coronary artery 43 and posterior descending coronary artery 45, to reduce the possibility of vascular damage during application of the high voltage defibrillating shocks to the electrodes. The patch electrode 15 is also configured such that the left circumflex coronary artery lies immediately above it when that electrode is in place.

Figure 1A:
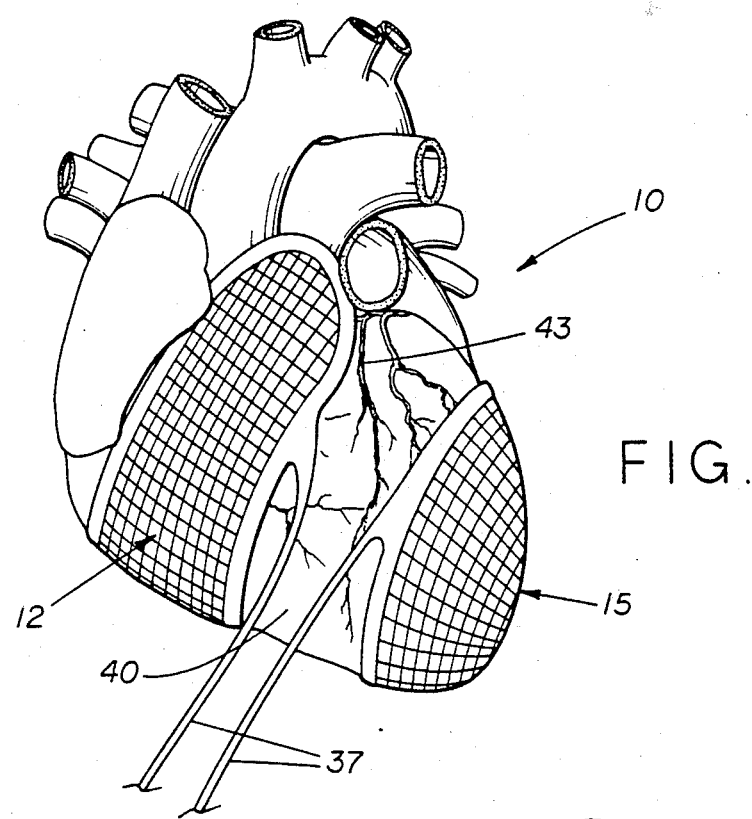
FIGS. 1a and 1b are diagrammatic representations of contoured patch electrodes according to the invention, in place on the heart seen from anterior and posterior views, respectively.
Figure 1B:
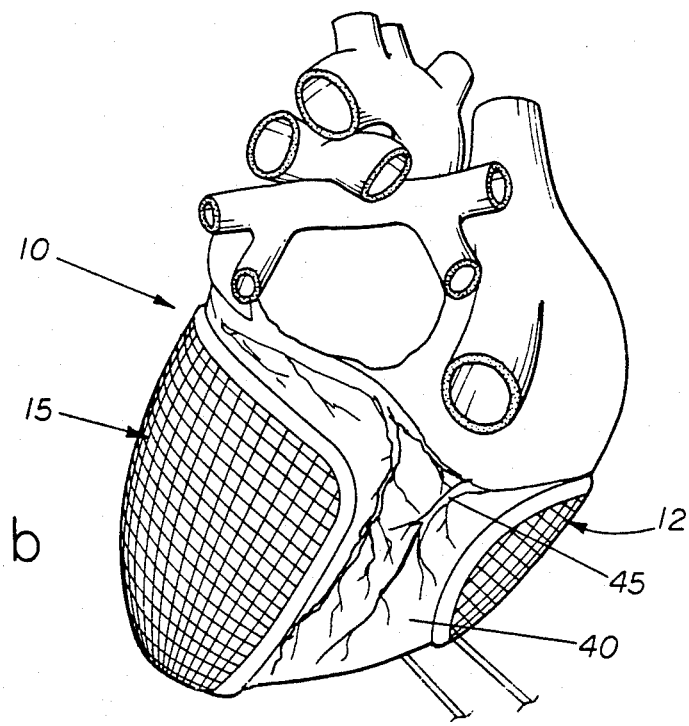
Figure 2A:
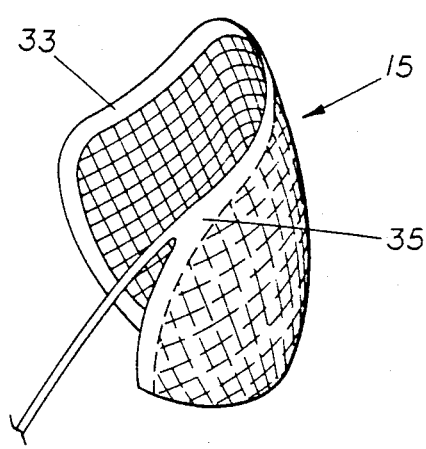
FIGS. 2a and 2b are perspective views of the contoured patch electrodes of FIG. 1, as seen prior to placement over the ventricles.
Figure 2B:
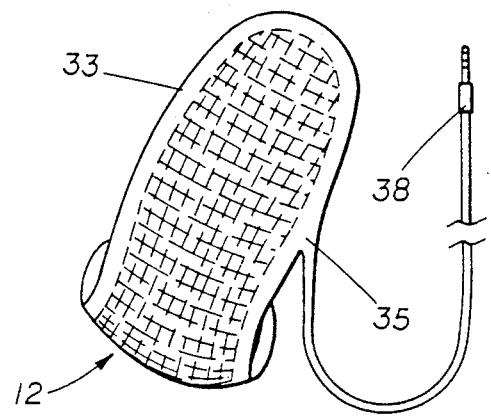

It should be noted that the patch electrodes of the present invention have a very large amount of their surface area at the base of the heart where the spaces are largest. Also, each electrode is shaped such that when viewed between the egdes of the two patches, most of the ventricles lie in a straight line betwen the patches, with the angle between that line and the patch electrodes being in the range from about 60 to about 80 degrees. Thus, the electrode system and configuration of each electrode provides good coverage of the base of the heart. However, it is hypothesized that improved results may also be attained relative to prior art defibrillation electrode systems even if somewhat smaller patch electrodes than those depicted in FIGS. 1a and 1b are employed, provided the design and placement principles and guidelines set forth herein are followed to a reasonable extent. Contoured patch electrodes may be designed in two or three sizes to capture the vast majority of the patient population.

It was observed that fibrillation tends to resume, after application of a shock just below the defibrillation threshold and, thus, not quite strong enough to defibrillate, in the area where the electric field produced by the electrode configuration is the weakest. The best (most successful) shock appears to be that which produces the highest energy level suitable to arrest fibrillation at the weakest portion of the field. The design philosophy for the electrodes of the present invention takes this into account in terms of the efficiency of the electrode system in delivering energy from the defibrillating waveform to the ventricles. If it were imagned that the edges of the two patch electrodes were the rims or openings at top and bottom of a lampshade, and those edges in confronting or opposing relationship were connected everywhere with straight lines perpendicular thereto, the objective is to minimize (within limits according to the design principles herein) the volume of the ventricles lying outside the boundaries of the imaginary cloth covering the lampshade between the two rims. This is based to an extent on field theory. Those portions of the ventricles outside the electrodes will be subjected to considerably less current density than the portion within the electrodes.

Figure 6A:
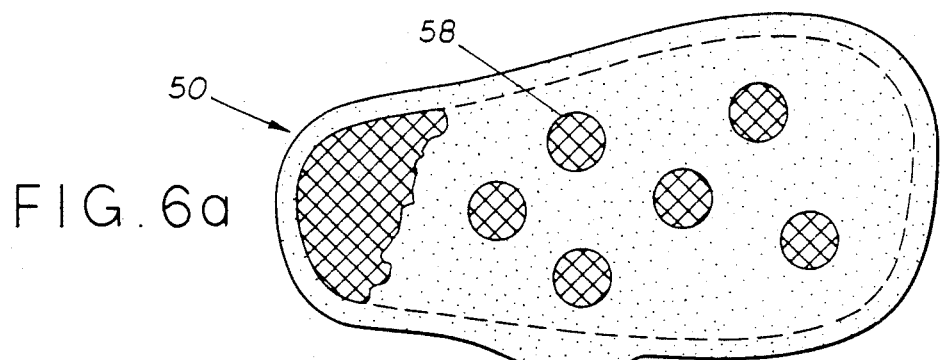
Figure 6B:
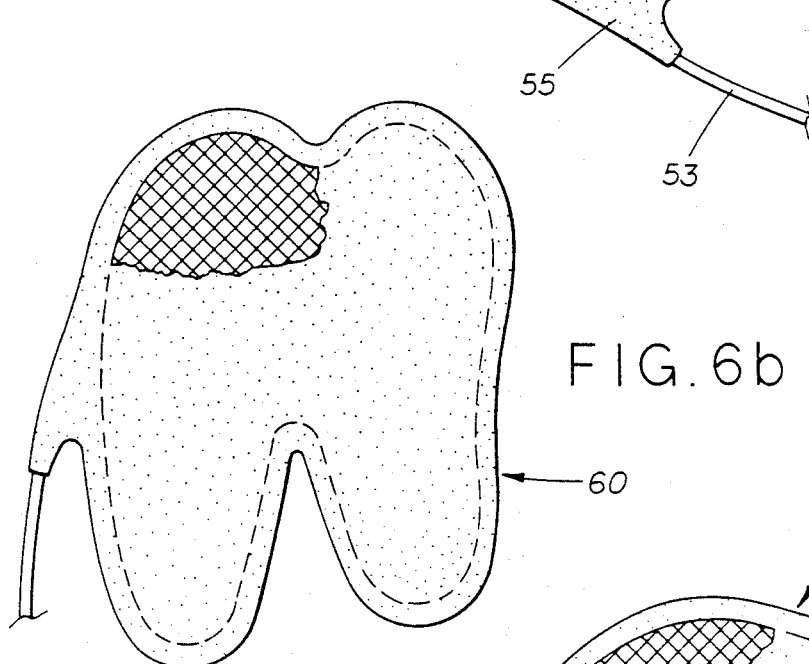
Figure 6C:
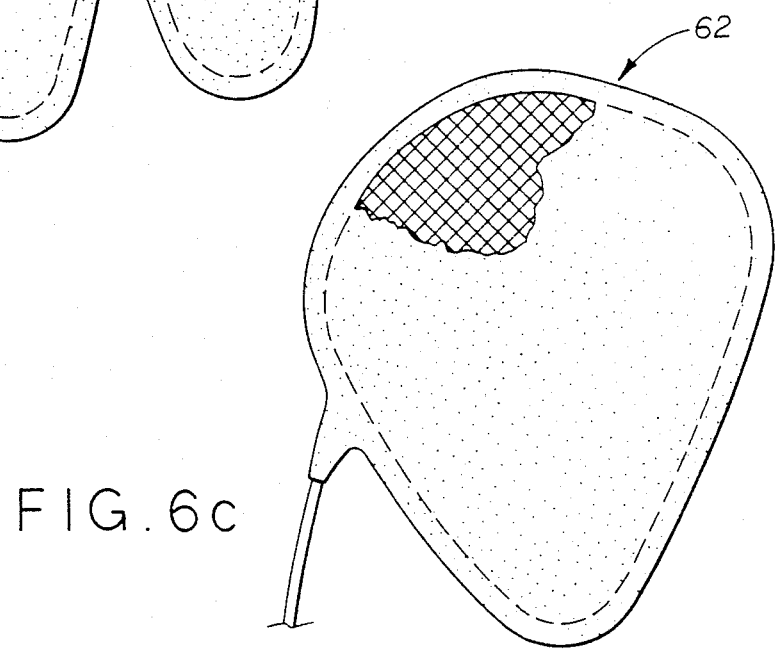

Referring now to FIG. 6, an alternative embodiment of the patch electrodes of the present invention, is that in which the electrodes are fabricated in the multilayer configuration described above, but are of a flat planar form and, therefore, readily flexed to assume the shape of the heart in the region of the respective ventricles over which they are to be placed, although it will be apparent that some deformation of such electrodes will occur in that placement. A right ventricular patch electrode 50 is shown in FIG. 6a, with the connection to lead 53 at a site 55 selected to assure that the lead will be positioned at the anterior of the heart when electrode 50 is in place, in the same manner as shown in FIG. 1a. It will be observed that patch electrode 50 has an outline similar to that of a shoe, or a thong.

According to another feature of the invention, electrode 53 is provided with one or more holes 58 through the insulative backing, but not through the conductive mesh. Each of the other flat patch electrodes of FIGS. 6b and c, and the previously described contoured patch electrodes 12 and 15 may similarly be provided with such holes in the insulative backing. The holes may be, and preferably are, larger than those shown in FIG. 6a; indeed, a single relatively large hole may be more desirable. Should the internal implanted defibrillator fail, the presence of one or more large holes in the insulative backing will allow current flow therethrough and in the heart, thereby lowering the threshold energy for transthoracic external defibrillation. The holes also serve to allow fluid egress and ingress through the electrode.

Two different shapes for a left ventricular flat patch electrode are shown in FIGS. 6b and c. Here again, these electrodes are constructed in a manner similar to that for the contoured patch electrodes, except that since electrodes 60 and 62 are flat, they tend to be more flexible and to assume the shape of the heart in the region of placement, albeit with some slight buckling of the electrode. Patch electrode 60 has an outline similar to that of a molar, while the outline of electrode 62 resembles that of a skull. In any event, the flat patch electrodes are basically designed according to the same design principles as applied to the contoured electrodes, including large surface area, capturing substantially all of the ventricular myocardium therebetween except in the region of the gap between opposing borders of the electrodes when placed over the ventricles. Electrode 60 is preferred as the flat version of the LV patch because it readily assumes the proper contour when the "roots" of the "molar" are brought together to provide a uniform gap 63 therebetween. They may be secured in that position using a soft silicone rubber strip 64, with subsequent curing.

As noted earlier herein, a wide range of thresholds for direct defibrillation using a variety of configurations has been reported in the literature. The initial shock strength used with currently available automatic implantable defibrillators is about 25 joules. In 1978, Mirowski et al. reported obtaining defibrillation thresholds (DFTs) of 4–10 joules with chronically implanted titanium catheter electrodes and epicardial defibrillation patches in dogs. In 1986, Kallok et al. reported obtaining a mean DFT of less than 3 joules in isolated dog hearts using large titanium patch electrodes in conjunction with a defibrillating catheter.

We have found in our studies that defibrillation is reliably achieved at shock energy levels considerably lower than those heretofore required, using defibrillation patch electrodes as described herein with defibrillation waveforms of various types. It will be observed from FIG. 7, which was derived from tests on six dogs using monophasic and biphasic waveforms, that the best results were obtained using biphasic waveforms of certain types. The results for waveforms 67, 70 and 71 were obtained with contoured patch electrodes secured to the epicardium, and the results for waveforms 68, 69 70 add 72 were obtained with the contoured electrodes affixed directly to the pericardium. The numbers below each waveform indicate duration of each phase in milliseconds.

The generating apparatus for and specific characteristics of these biphasic waveforms are disclosed in other patent applications assigned to the same assignee as is the present application, and form no part of the invention disclosed herein.

Although there are differences in the DFTs for the different waveforms, in FIG. 7 and other compatible test results not shown herein, the DFTs achieved in these tests are much lower throughout than those reported to date by others. Indeed, known defibrillation electrode systems currently employed are consistently successful in the 7 to 10 joule range; energy levels which are to be contrasted with the DFTs consistently demonstrated in the 2.0 to 3.0 joule range with electrode configuration and placement according to the present invention, and which are attributable virtually solely to the electrode system.

While certain preferred embodiments of defibrillator patch electrodes have been disclosed herein, it will be apparent from consideration of the disclosure that variations and modifications may be provided without departing from the principles and guidelines of the invention. Accordingly, the invention is to be limited only to the extent required by the appended claims.

We claim:

1. A pair of implantable defibrillation patch electrodes to deliver defibrillation shocks to the heart, comprising
   a first patch electrode contoured to fit over and substantially conform to the shape of the right ventricle of the heart,
   a second patch electrode contoured to fit over and substantially conform to the shape of the left ventricle of the heart in spaced relationship to the first patch electrode to form a substantially equidistant gap between confronting borders of the two patch electrodes in the region along the ventricular septum,
   each of the patch electrodes including means for delivering the defibrillation shocks to the respective electrodes, and
   each of the patch electrodes being of a size and shape to encompass a substantial portion of the respective ventricular myocardium within the borders of the respective patch electrode, to establish a substantially uniform potential gradient field throughout the entire ventricular mass when a defibrillation shock is delivered to the electrodes.

2. The pair of defibrillation patch electrodes of claim 1, in which
   the said gap between the confronting borders of the two patch electrodes is sufficiently wide to limit shunting of current between the edges of the electrodes along said borders upon delivery of a defibrillation shock to the pair.

3. The pair of defibrillation patch electrodes of claim 2, in which
   each of the patch electrodes has a size and shape to accommodate the ventricular septum in the said gap between the confronting borders of the two patch electrodes, to establish preferential current flow through one ventricle across the septum to the free wall of the other ventricle when a defibrillation shock is delivered to the electrodes.

4. The pair of defibrillation patch electrodes of claim 3, in which
   each of the patch electrodes has a size and shape to accommodate a substantial portion of each of the right and left coronary arteries in the said gap between the confronting borders of the two patch electrodes, to avoid vascular damage as a consequence of the delivery of defibrillation shocks to the electrodes.

5. The pair of defibrillation patch electrodes of claim 1, in which
   each of the patch electrodes comprises a conductive mesh adapted to lie closest to the surface of the respective ventricle, a flexible biocompatible insulative backing covering the opposite side of the mesh, and a resilient bicompatible insulative border layer means about each electrode for suturing the respective electrode to the epicardium.

6. The pair of defibrillation patch electrodes of claim 5, in which
   each of the electrodes has at least one hole to permit flow of body fluid therethrough.

7. An electrode system for use in defibrillating the heart, comprising
   a first patch electrode configured for placement directly over the surface of the right ventricle of the heart,
   a second patch electrode configured for placement directly over the surface of the left ventricle of the heart in spaced relationship to the first patch electrode to form a relatively uniform gap between confronting borders of the two patch electrodes throughout the region of the ventricular septum when the electrodes are in place over the respective ventricles, and
   connecting means for application of electrical energy to the respective electrodes to defibrillate the heart,
   the patch electrodes having respective sizes and shapes to encompass virtually the entire ventricular myocardium therebetween, toward establishing a uniform potential gradient throughout the entire ventricular mass upon application of electrical energy to the electrodes, with the said gap between the confronting borders of the patch electrodes being sufficiently wide to avoid shunting of current across those borders and to accommodate at least some of the major coronary arteries therebetween.

8. The electrode system according to claim 7, in which
   the ventricular septum lies within the said gap between the confronting borders of the patch electrodes when the electrodes are in place over the respective ventricles.

9. The electrode system according to claim 8, in which
   each of the electrodes comprises a conductive mesh adapted to lie adjacent to the surface of the respective ventricle, and a flexible biocompatible insulative backing covering the opposite side of the mesh.

10. The electrode system according to claim 9, in which
    each of the electrodes further has a resilient biocompatible insulative border about the entire edge of the respective electrode for suturing thereof to either of the epicardium or the pericardium.

11. The electrode system according to claim 9, in which
each of the electrodes has a hole in the insulative backing.

12. The electrode system according to claim 7, in which
each of the electrodes is contoured to closely conform to the shape of the heart in the region of the ventricle over which the respective electrode is to be placed.

13. The electrode system according to claim 7, in which
each of the electrodes is flexible and has a normally flat configuration patterned with a shape which is adequate, when the electrode is in place over the respective ventricle, to encompass a substantial portion of the ventricular myocardium with some deformation of the electrode.

14. The method of making patch electrodes for use in defibrillating the heart, comprising the steps of
fashioning a first patch electrode including a conductive layer with an overlying adherent insulative layer, configured with a size and shape substantially conforming to and adequate for coverage of the majority of the right ventricular of the heart when in place over the surface thereof,
conductively fastening an electrical lead to the conductive layer in a limited area at the border thereof free of the insulative layer,
fashioning a second patch electrode including a conductive layer with an overlying adherent insulative layer, configured with a size and shape substantially conforming to and adequate for coverage of the majority of teh left ventricle of the heart when in place over the surface thereof,
conductively fastening an electrical lead to the conductive layer of the second patch electrode in a limited area at the border thereof free of the insulative layer, and
further sizing and shaping the first and second patch electrodes such that when they are in place over the respective ventricles a gap is formed between the confronting borders of the two electrodes along the ventricular septum, substantially equidistant throughout the region of the confrontation.

15. The method according to claim 14, in which
the sizing and shaping of the first and second patch electrodes is further such that the gap is sufficiently wide to limit shunting of current across the confronting borders of the two electrodes when the electrodes are energized with defibrillating shocks when in place over the respective ventricles.

16. The method according to claim 15, in which
the sizing and shaping of the first and second patch electrodes is further such that the gap between confronting borders of the two electrodes is sufficiently wide to accommodate the ventricular septum therein, so that preferential current flow will be through one ventricle across the septum to the free wall of the other ventricle when the electrodes are in place over the respective ventricles and defibrillation shocks are delivered thereto.

17. The method according to claim 16, in which
the sizing and shaping of the first and second patch electrodes is further such that the left anterior descending coronary artery and the posterior descending coronary artery will lie in the gap between the confronting borders of the two patch electrodes, to avoid vascular damage from the delivery of defibrillation shocks to the electrodes when in place over the respective ventricles.

18. The method according to claim 14, in which
the conductive layer is a mesh, and further including the step of forming a hole in the insulative backing.

19. The method according to claim 14, in which
the first and second patch electrodes are fashioned with a contour to conform to the shape of the heart in the region of the respective ventricles over which the electrodes are to be placed.

20. The method according to claim 14, in which
the first and second patch electrodes are flexible and fashioned with a flat configuration and a size and shape such that when placed over the respective ventricles each will encompass a substantial portion of the ventricular myocardium with some deformation of the electrode.

* * * * *